May 14, 1974 E. CULLY Plant Pat. 3,548
POND CYPRESS
Filed Dec. 27, 1971
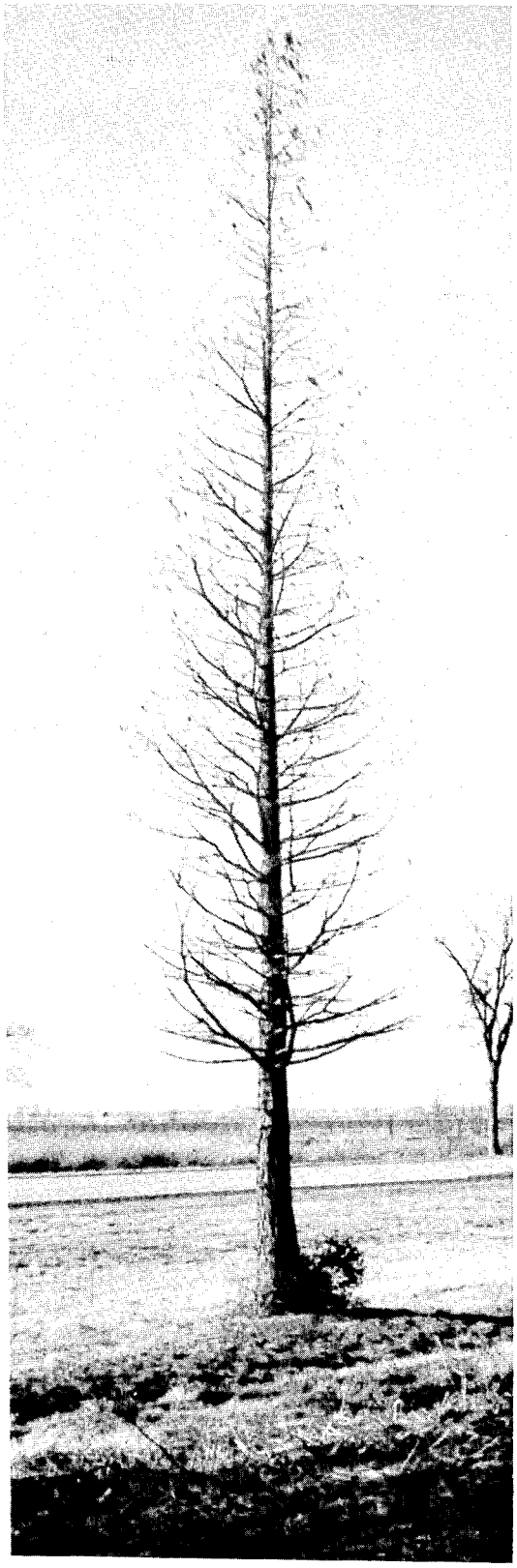
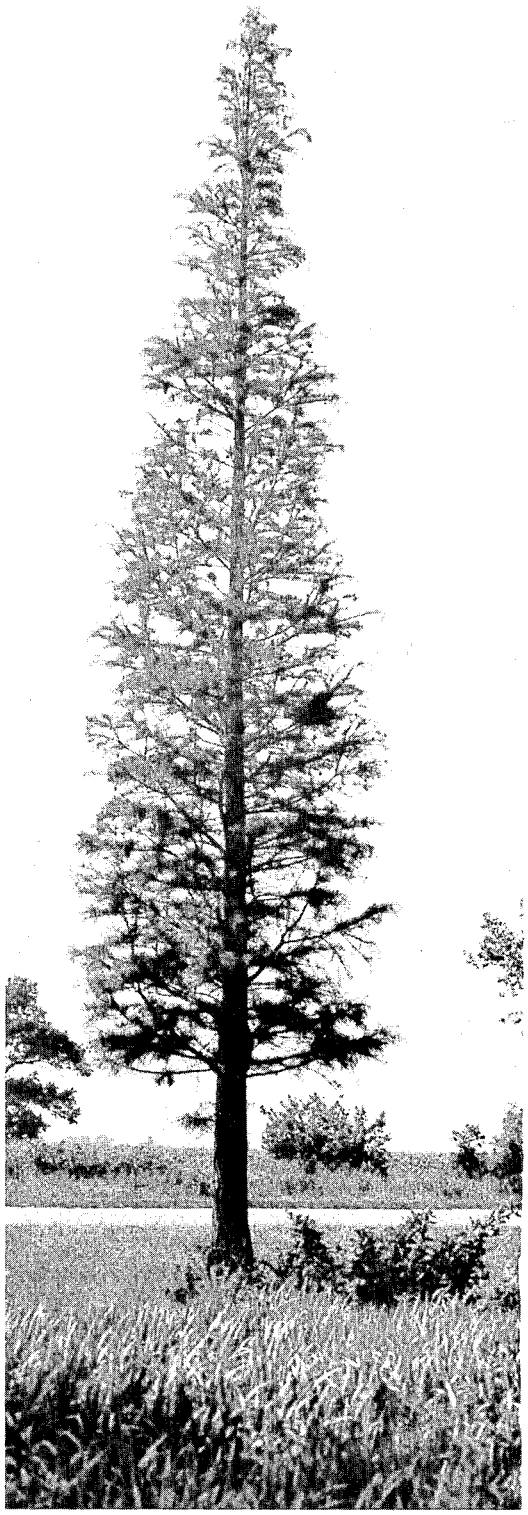

United States Patent Office

Plant Pat. 3,548
Patented May 14, 1974

3,548

POND CYPRESS TREE

Earl Cully, R.R. 5, Jacksonville, Ill. 62650

Filed Dec. 27, 1971, Ser. No. 212,826
Int. Cl. A01h 7/00
U.S. Cl. Plt.—50 1 Claim

ABSTRACT OF THE DISCLOSURE

This disclosure concerns a new and distinct variety of Gymnospermae, Pinacea (Taxodiacea), commonly known as a pond cypress, characterized by its rapid growth, its distinctive growth of the numerous primary branches which leave the main stem at an angle of 65 to 70 degrees below vertical, its uniform short branch length, with the length of its longer branches not exceeding about one-twelfth of the tree height.

BACKGROUND OF THE INVENTION

This new variety of pond cypress was discovered by me in southeastern Illinois, in White County, on cultivated property. During the past two years, I have grafted many cuttings from this parent tree at Cully Nursery in Jacksonville, Illinois, on *Taxodium distichium* under stock. At present, I have over 1,000 grafts growing true to form and they are rapid growers.

DESCRIPTION OF THE DRAWING

FIG. 1 shows my new variety in fully leaved form; and FIG. 2 shows my new variety without leaves.

DESCRIPTION OF THE NEW PLANT VARIETY

The following is a detailed description of my new variety of pond cypress.

Origin: Seedling.
Parentage: Unknown.
Classification: Gymnospermae, Pinaceae (Taxodiaceae)
*Botanic.*—*Taxodium ascendens* (Brongniart).
Form: Tree.
Shape: Narrow conical.
Height: 60 feet at approximately 30 years.
Trunk size:
13½ inches at breast height at 30 years.
19 inches at ground level at 30 years.
Growth rate: Rapid for its species—about two feet in height per year.
Branches:
*Angle of attachment.*—60 to 70 degrees below the vertical.
*Spacing.*—Dense 15 to 18 inches apart.
*Size.*—To 5 feet long.
*Bark.*—Green on young branches; brown on older and on larger (perennial) branches by summer. Annual branches arise from buds on previous year's older branches. They are green through growing season, very slender, usually under 10 centimeters long, but occasionally more than 20 centimeters long, arranged radially around the branch and tend to hang downwardly.

Leaves:
*Length.*—To 8 millimeters.
*Width.*—Under ½ millimeter.
*Form.*—Subulate, appressed and incurred toward branchlet.
*Quantity.*—Abundant, in length overlapping each other around branchlets.
*Color.*—Soft, bright green, turning orange brown before falling.
Green color of leaves and branchlets is retained through growing season.
Thorns, spines or prickles: None.
Flowers: Male and female strobiles typical for the species.
*Blooming period.*—March and April.
Fruit: A cone typical of the species.
*Sizes.*—Axial diameter: 1.8 to 3.3 centimeters. Transverse diameter: 1.8 to 2.6 centimeters.
*Form.*—Globose or obovoid composed of adherent scales.

This new variety most resembles *T. ascendens nutans* (Ait) Rehder, the oldest named variety in the species (named in 1789) and the only one listed in A. Rehder's "Manual of Cultivated Trees and Shrubs" (Ed. 2, 1940, Macmillan), which has pendulous branches but does not resemble the present variety in growth habit.

This variety has been compared with other seedlings and grafted trees in its species, including wild trees in its native range (in Georgia, Florida and Alabama), planted seedlings in Illinois, Indiana and Pennsylvania, and another grafted clone (from Morris Arboretum, Philadelphia, Pennsylvania) and in the Cully Nursery at Jacksonville, Illinois, over a period of four years, but distinguished therefrom by its rapid growth, the distinctive angle of the numerous primary branches extending at an angle of from 65 to 70 degrees below the vertical, and very uniformly short branch length, the longer branches not exceeding one-twelfth of the tree height.

I claim:

1. A new and distinct variety of pond cypress tree [Gymnospermae, Pinaceae (Taxodiacea)] substantially as shown and described, characterized by its rapid height growth, the distinctive angle of the numerous primary branches extending at an angle of from 65 to 70 degrees below the vertical, the very uniformity short branch length, the longer branches not exceeding one-twelfth of the tree height.

References Cited

The First Plant Patents, Allyn, Educ. Found. Inc., 1934, pp. 67–69 relied on.

The Standard Cyclo. Bailey, 1935, p. 3314 relied on.

Trees for Amer. Gard., Wyman, 1951, p. 327 relied on.

New Illus. Ency. of Gard., Everett, 1960, p. 2249 relied on.

Manual of Cultivated Trees and Shrubs," Rehder, 1960, p. 49 relied on.

ROBERT E. BAGWILL, Primary Examiner